United States Patent [19]
Woltersdorf, Jr. et al.

[11] 4,291,050
[45] Sep. 22, 1981

[54] 6,7-DISUBSTITUTED-2 OR 2,2-SUBSTITUTED-5-SUBSTITUTED-1-INDANONES

[75] Inventors: Otto W. Woltersdorf, Jr., Chalfont; Edward J. Cragoe, Jr., Lansdale, both of Pa.

[73] Assignee: Merck & Co., Inc., Rahway, N.J.

[21] Appl. No.: 50,851

[22] Filed: Jun. 21, 1979

[51] Int. Cl.$^3$ .................... A61K 31/335; C07C 49/67
[52] U.S. Cl. ........................... 424/278; 260/340.9 R; 562/471; 564/428; 568/327; 424/317; 424/330; 424/331
[58] Field of Search ...... 260/586 FA, 570.7, 340.9 R; 562/471; 424/278, 317, 330, 331; 568/327; 564/428

[56] References Cited

U.S. PATENT DOCUMENTS

| | | | |
|---|---|---|---|
| 2,881,218 | 4/1959 | Kundiger et al. | 260/590 FA |
| 3,822,310 | 7/1974 | Shen et al. | 260/590 FA |
| 3,950,408 | 4/1976 | Chamberlin et al. | 260/590 FA |
| 4,065,456 | 12/1977 | Nakagawa et al. | 260/590 FA X |
| 4,081,554 | 3/1978 | Cragoe, Jr. et al. | 260/559 B X |
| 4,096,267 | 6/1978 | Cragoe, Jr. et al. | 260/559 B X |

*Primary Examiner*—Ethel G. Love
*Attorney, Agent, or Firm*—Raymond M. Speer; M. C. Sudol, Jr.

[57] ABSTRACT

This invention relates to a new class of chemical compounds which can be described generally as 6,7-disubstituted-2 or 2,2-substituted-5-substituted-1-indanones. These compounds are effective diuretic and saluretic agents.

6 Claims, No Drawings

6,7-DISUBSTITUTED-2 OR 2,2-SUBSTITUTED-5-SUBSTITUTED-1-INDANONES

BACKGROUND OF THE INVENTION

This invention relates to a new class of chemical compounds which can be described generally as 6,7-disubstituted-2 or 2,2-substituted-5-substituted-1-indanones. Pharmacological studies show that the instant products are effective diuretic and saluretic agents which can be used in the treatment of conditions associated with electrolyte and fluid retention and hypertension.

When administered in therapeutic dosages, in conventional vehicles, the instant products effectively reduce the amount of sodium and chloride ions in the body, lower dangerous excesses of fluid levels to acceptable levels and in general, alleviate conditions usually associated with edema.

Use of the instant compounds for the pharmacological utility stated over the carboxylic acids, esters or amides of these compounds (described in U.S. Pat. Nos. 4,081,552 and 4,096,267) result in a longer duration of action in the body, are neutral in the gastro-intestinal tract and have a different distribution pattern in the body although they are eventually converted to the products described in U.S. Pat. Nos. 4,081,552 and 4,096,267.

The above invention are compounds having the following structural formula:

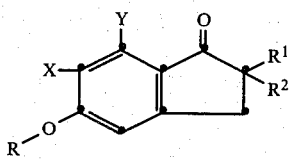

wherein
x is halo (Cl, Br, I or F) or methyl;
Y is halo (Cl, Br, I or F) or methyl;
$R^1$ is hydrogen or $C_{1-6}$ alkyl;
$R^2$ is
  $C_{1-6}$ alkyl, $C_{3-6}$ cycloalkyl,
  aryl particularly phenyl,
  aralkyl particularly benzyl and substituted phenyl wherein the substituent is $C_{1-3}$ alkyl or halo (Cl, Br or I); and
R is
  hydroxy ethyl;
  2-oxo propyl;
  1,2-dihydroxypropyl;
  amino ethyl;
  formyl methyl;
  dialkoxy ($C_{1-6}$) methyl;
  dicarboxy methyl; or

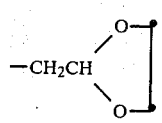

A preferred embodiment of this invention relates to compounds of Formula I wherein
R is 2-oxy propyl or hydroxy ethyl;
$R^1$ is alkyl $C_{1-6}$;
$R^2$ is cycloalkyl $C_{3-6}$ or phenyl and
X and Y are chloro.

The compounds of Formula I are conveniently prepared according to the following equation:

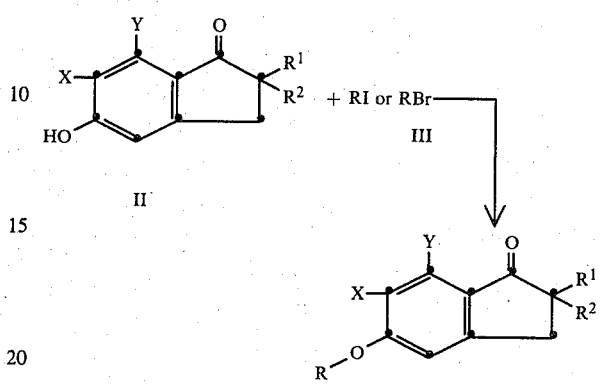

wherein X, Y, R, $R^1$ and $R^2$ are as previously defined. Thus, 5-hydroxy-1-indanones of Formula II (whose preparation are shown in U.S. Pat. Nos. 4,081,552 and 4,096,267) are reacted with a halogenated compound of Formula III in the presence of a base to yield the desired product.

The reaction conditions are not critical and the reaction is carried out with an excess of Compound III, preferably in an inert organic solvent such as dimethylformamide, acetone or alcohol. The reaction is generally run at from 25° C. to the reflux temperature of the solvent used and generally for a period of from 1-24 hours.

The product I is isolated from the reaction mixture by known methods such as by extraction with ethyl ether and evaporation of the extracting solvent.

The novel compounds of this invention are diuretic and saluretic agents which can be administered in a wide variety of therapeutic dosages in conventional vehicles as, for example, by oral administration in the form of a tablet or by intravenous injection. Also, the daily dosage of the products may be varied over a wide range as, for example in the form of scored tablets containing 5, 10, 25, 50, 100, 150, 250 and 500 milligrams of the active ingredient for the symptomatic adjustment of the dosage to a patient to be treated. These dosages are well below the toxic or lethal dose of the products. Generally the dosage range is 5 mg to 2,000 mg per day per patient with a preferred dosage range of 5 to 1000 mg per day.

A suitable unit dosage form of the proucts of this invention can be administered by mixing 100 milligrams of a compound of Formula I with 99 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employes. Compressed tablets, pills, or other desired unit dosages can be prepared to incorporate the compounds of this invention by conventional methods and, if desired, can be made up as elixirs or as injectable solutions by methods well known by pharmacists.

It is also within the scope of this invention to combine two or more of the compounds of this invention in a unit dosage form or to combine one or more of the compounds of this invention with other known diuretics and saluretics or with other desired therapeutic and/or nutrative agents in dosage unit form.

The examples which follow are illustrative only and it will be apparent to those having ordinary skill in the art that all of the products embraced by Formula I, supra, may also be prepared in an analogous manner by substituting the appropriate starting materials for those set forth in the examples.

EXAMPLE 1

6,7-Dichloro-2-methyl-5-(2-oxopropoxy)-2-phenyl-1-indanone

A solution containing chloroacetone (11 g., 0.12 mole) and potassium iodide (0.5 g.) in acetone (30 ml) is stored in the dark for 18 hours then added in portions over a one hour period to a stirred refluxing mixture of 6,7-dichloro-5-hydroxy-2-methyl-2-phenyl-1-indanone (24.5 g., 0.08 mole) and potassium carbonate (11.0 g., 0.08 mole) in acetone. The acetone is distilled at reduced pressure and the residue slurried with ether and water to give 6,7-dichloro-2-methyl-5-(2-oxopropoxy)-2-phenyl-1-indanone which melts at 144° C. after recrystallization from ethanol.

Elemental Analysis for $C_{19}H_{16}Cl_2O_3$; Calc.: C, 62.82; H, 4.44; Found: C, 62.57; H, 4.74.

EXAMPLE 2

2-(6,7-Dichloro-2-methyl-1-oxo-2-phenyl-5-indanyloxy)ethanol

To a solution of sodium (1.76 g., 0.076 g. atom) in 1-propanol (250 ml.) is added 6,7-dichloro-5-hydroxy-2-methyl-2-phenyl-1-indanone (23.5 g., 0.076 mole) and 2-iodoethanol (14.5 g., 0.085 mole). The reaction mixture is refluxed 18 hours then evaporated at reduced pressure to give 12.0 g of 2-(6,7-dichloro-2-methyl-1-oxo-2-phenyl-5-indanyloxy)ethanol which melts at 188°–90° C. after recrystallization from ethanol.

Elemental Analysis for $C_{18}H_{16}Cl_2O_3$; Calc.: C, 61.55; H, 4.59; Found: C, 61.23; H, 4.57.

EXAMPLE 3

Dry-filled capsules containing 50 mg. of active ingredient per capsule

| | Mg. per capsule |
|---|---|
| 6,7-Dichloro-2-methyl-5-(2-oxo-propoxy)-2-phenyl-1-indanone | 50 |
| Lactose | 149 |
| Magnesium stearate | 1 |
| Capsule (size No. 1) | 200 |

The 6,7-dichloro-2-methyl-5-(2-oxopropoxy)-2-phenyl-1-indanone is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

It will be apparent from the foregoing description that the compounds of Formula I constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A compound of the formula

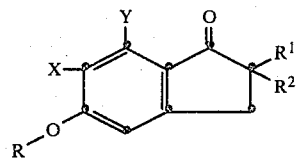

wherein
X is halo or methyl
Y is halo or methyl;
R is
  hydroxy ethyl;
  2-oxo propyl;
  1,2-dihydroxypropyl, provided that X or Y is not methyl;
  amino ethyl;
  formyl methyl;
  dialkoxy ($C_{1-6}$) methyl; or

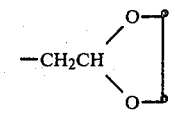

$R^1$ is hydrogen or $C_{1-6}$alkyl;
$R^2$ is $C_{1-6}$alkyl, $C_{3-6}$cycloalkyl, aryl, aralkyl or substituted aryl wherein the substituent is halo or $C_{1-3}$ alkyl.

2. A compound of the formula

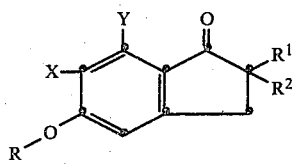

wherein
X and Y are chloro;
R is 2-oxy propyl or hydroxy ethyl;
$R^1$ is $C_{1-6}$ alkyl;
$R^2$ is $C_{3-6}$ cycloalkyl or phenyl.

3. A compound of claim 2 which is 6,7-dichloro-2-methyl-5-(2-oxopropoxy)-2-phenyl-1-indanone.

4. A compound of claim 2 which is 2-(6,7-dichloro-2-methyl-1-oxo-2-phenyl-5-indanyloxy)ethanol.

5. A pharmaceutical composition useful in the treatment of edema and hypertension which comprises a anti-edema and hypertensive effective amount of a compound of the formula

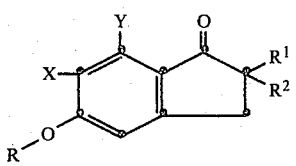

wherein
X is halo or methyl

Y is halo or methyl;
R is
   hydroxy ethyl;
   2-oxo propyl;
   1,2-dihydroxypropyl, provided that X or Y is not methyl;
   amino ethyl;
   formyl methyl;
   dialkoxy (C$_{1-6}$) methyl; or

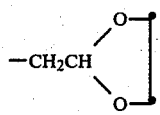

R$^1$ is hydrogen or C$_{1-6}$alkyl;
R$^2$ is C$_{1-6}$ alkyl, C$_{3-6}$ cycloalkyl, aryl, aralkyl or substituted aryl wherein the substituent is halo or C$_{1-3}$ alkyl
and a pharmaceutically inert carrier.

6. A method of treating edema and hypertension which comprises administering to a patient in need of such treatment a anti-edema and hypertensive effective amount of a compound of the formula:

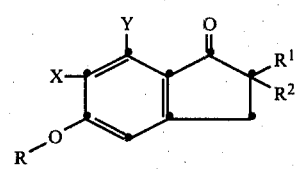

wherein
   X is halo or methyl
   Y is halo or methyl;
   R is
      hydroxy ethyl;
      2-oxo propyl;
      1,2-dihydroxypropyl, provided that X or Y is not methyl;
      amino ethyl;
      formyl methyl;
      dialkoxy (C$_{1-6}$) methyl; or

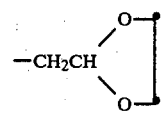

R$^1$ is hydrogen or C$_{1-6}$alkyl;
R$^2$ is C$_{1-6}$ alkyl, C$_{3-6}$ cycloalkyl, aryl, aralkyl or substituted aryl wherein the substituent is halo or C$_{1-3}$ alkyl.

* * * * *